United States Patent
Van Der Heide et al.

(10) Patent No.: US 10,111,593 B2
(45) Date of Patent: Oct. 30, 2018

(54) MONITORING SYSTEM FOR MONITORING A PATIENT AND DETECTING DELIRIUM OF THE PATIENT

(71) Applicant: KONINKLIJKE PHILIPS N.V., Eindhoven (NL)

(72) Inventors: Esther Marjan Van Der Heide, Nijmegen (NL); Adrienne Heinrich, Den Bosch (NL); Thomas Falck, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 818 days.

(21) Appl. No.: 14/348,078

(22) PCT Filed: Sep. 28, 2012

(86) PCT No.: PCT/IB2012/055178
§ 371 (c)(1),
(2) Date: Mar. 28, 2014

(87) PCT Pub. No.: WO2013/050912
PCT Pub. Date: Apr. 11, 2013

(65) Prior Publication Data
US 2014/0235969 A1 Aug. 21, 2014

Related U.S. Application Data

(60) Provisional application No. 61/544,321, filed on Oct. 7, 2011.

(51) Int. Cl.
H04N 9/47 (2006.01)
A61B 5/00 (2006.01)
(Continued)

(52) U.S. Cl.
CPC .......... *A61B 5/0064* (2013.01); *A61B 5/0476* (2013.01); *A61B 5/053* (2013.01);
(Continued)

(58) Field of Classification Search
CPC ..................................................... A61B 5/0064
USPC ......... 348/77; 434/236; 340/573.1; 345/156; 600/300, 301
See application file for complete search history.

(56) References Cited

U.S. PATENT DOCUMENTS 6,049,281 A * 4/2000 Osterweil ............ A61B 5/1128
340/573.1
6,774,885 B1 * 8/2004 Even-Zohar ......... A61B 5/1036
345/156

(Continued)

OTHER PUBLICATIONS

Aldhous, P.; In hospital, am losing my mind; 2011; New Scientist; pp. 6-7.

(Continued)

*Primary Examiner* — Gims S Philippe (57) ABSTRACT

The present invention relates to a monitoring system (1, 2, 3) and a corresponding monitoring method for monitoring a patient and detecting delirium of the patient in an unobtrusive manner without the need of on-body sensors. The proposed monitoring system comprises a monitoring unit (10) for obtaining image data (30) of the patient over time, an image analysis unit (12) for detecting motion events of the patient from the obtained image data (30), an evaluation unit (14) for classifying the detected motion events into delirium-typical motion events and non-delirium-typical motion events, and a delirium determination unit (16) for determining a delirium score (32) from the duration, intensity, type, location and/or occurrence of delirium-typical motion events, said delirium score (32) indicating the likelihood and/or strength of delirium of the patient.

20 Claims, 3 Drawing Sheets

(51) Int. Cl.
*A61B 5/0476* (2006.01)
*A61B 5/11* (2006.01)
*A61B 5/16* (2006.01)
*A61B 5/053* (2006.01)

(52) U.S. Cl.
CPC ............ *A61B 5/1128* (2013.01); *A61B 5/165* (2013.01); *A61B 5/4088* (2013.01); *A61B 5/7282* (2013.01); *A61B 5/0077* (2013.01); *A61B 5/1113* (2013.01); *A61B 5/1116* (2013.01); *A61B 5/1118* (2013.01); *F04C 2270/041* (2013.01)

(56) References Cited

U.S. PATENT DOCUMENTS

| | | | |
|---|---|---|---|
| 6,893,407 B1 * | 5/2005 | Brooks | G06F 3/016 600/300 |
| 2002/0143240 A1 | 10/2002 | Teicher et al. | |
| 2009/0005648 A1 | 1/2009 | Teicher et al. | |
| 2010/0041968 A1 * | 2/2010 | Meschisen | G06F 19/321 600/301 |
| 2010/0049095 A1 | 2/2010 | Bunn et al. | |
| 2010/0280336 A1 | 11/2010 | Giftakis et al. | |
| 2011/0207098 A1 * | 8/2011 | Jakovljevic | A61B 5/6804 434/236 |

OTHER PUBLICATIONS

Heinrich, A., et al.; Body movement analysis during sleep based on video motion estimation; 2013; IEEE Trans. on e-Health Networking, Applications & Services; pp. 539-543.

Van Den Boogaard, M., et al.; Development and validation of PRE-DELIRIC (PREdiction of DELIRium in ICu patients) delirium prediction model for intensive care patients: observational multicentre study; 2012; BMJ; 344:e420; 11 pages.

* cited by examiner

MONITORING SYSTEM FOR MONITORING A PATIENT AND DETECTING DELIRIUM OF THE PATIENT

CROSS REFERENCE TO RELATED APPLICATIONS

This application is a national filing of PCT application Serial No. PCT/IB2012/055178, filed Sep. 28, 2012, published as WO 2013/050912 A1 on Apr. 11, 2013, which claims the benefit of U.S. provisional application Ser. No. 61/544,321 filed Oct. 7, 2011, which is incorporated herein by reference,

FIELD OF THE INVENTION

The present invention relates to a monitoring system and a corresponding monitoring method for monitoring a patient and detecting delirium of the patient. Further, the present invention relates to a processor and a corresponding processing method for use in such a monitoring system. Still further, the present invention relates to a computer program for implementing said processing method.

BACKGROUND OF THE INVENTION

Delirium is a neuropsychiatric syndrome with a multifactorial etiology that occurs in a majority of ICU (Intensive Care Unit) patients. Delirium is associated with increased mortality, prolonged hospital stay, and long term effects such as decreased independent living, increased rate of institutionalization and increased risk to develop long-term cognitive impairment. Longer hospital stay and complications associated with delirium in the ICU lead to significantly higher costs of care. The prevalence rates of delirium in an ICU range from 11% to 87%. Accurate and early detection and treatment of delirium is the key to improving patient outcome and curbing delirium-related health care costs.

Currently, for the diagnosis of delirium in ICU patients a couple of validated screening questionnaires (such as CAM-ICU) are used. With these methods patients are checked at most three times a day. With the fluctuating character of delirium the delirious episodes are easily missed. Besides, under-detection of delirium is still the case even if screening instruments are used. Accurate and early detection methods may lead to more effective application of appropriate clinical interventions, leading to better outcome and reduced induced mortality. Hence, there is a need for a (semi-)automated, continuous and objective delirium monitoring system and method.

A disturbed motor activity pattern is a frequent manifested feature in delirious patients. Based on motoric alterations three clinical subtypes of delirium are distinguished: hyperactive, hypoactive and mixed. The definitions of the hypoactive, hyperactive and mixed motor subtypes are based on different psychomotor symptoms. A hyperactive delirium is characterized by increased quantity of motor activity, loss of control of activity, restlessness, and wandering. Patients with a hypoactive delirium demonstrate features such as decreased amount of activity, and decreased speed of actions. Patients with a mixed delirium shift between hypo- and hyperactivity.

Measurement of disturbed motor activity patterns to detect delirium is reported in a few studies. In these studies on-body accelerometer-based techniques were used to measure activity. Results showed that measurement of motoric alterations is a potential candidate for delirium detection.

The use of video monitoring for whole body motion detection was recently demonstrated by comparing video and wrist actigraphy for monitoring body movement in healthy subjects during sleep (Heinrich, A., van Vugt, H., A new video actigraphy method for non-contact analysis of body movement during sleep (2010), European Sleep Research Society ESRS, Journal on Sleep Research, vol. 19 (suppl. 2)). Motion data of both techniques corresponded for small, medium and large motions. Small and sometimes even medium movements were missed by conventional wrist actigraphy if the moving body part was not the one with the attached actigraphy system.

A disadvantage of wrist actigraphy methods is that it is measures the movements of the part of the body where it is attached to. So movements of other parts of the body are missed. Changes in motoric behavior are not limited to one part of the body, measurement of only one extremity might result in missed motions and as a consequence under-detection of delirium. Further, an extra on-body sensor might irritate or confuse patients.

SUMMARY OF THE INVENTION

It is an object of the present invention to provide a (semi-)automated, continuous and objective delirium monitoring system and method that avoid the above mentioned disadvantages. Further, a corresponding processor and processing method as well as a computer program shall be provided.

In a first aspect of the present invention a monitoring system for monitoring a patient and detecting delirium of the patient is presented comprising:
  a monitoring unit for obtaining image data of the patient over time,
  an image analysis unit for detecting motion events of the patient from the obtained image data,
  an evaluation unit for classifying the detected motion events into delirium-typical motion events and non-delirium-typical motion events, and
  a delirium determination unit for determining a delirium score from the duration, intensity, type, location and/or occurrence of delirium-typical motion events, said delirium score indicating the likelihood and/or strength of delirium of the patient.

In a further aspect of the present invention a processor is presented comprising:
  a first processing unit for detecting motion events of the patient from image data obtained over time from the patient,
  a second processing unit for classifying the detected motion events into delirium-typical motion events and non-delirium-typical motion events,
  a third processing unit for determining a delirium score from the duration, intensity, type, location and/or occurrence of delirium-typical motion events, said delirium score indicating the likelihood and/or strength of delirium of the patient.

In yet another aspect of the present invention, a computer program is provided which comprises program code means for causing a computer to perform the steps of the processing method when said computer program is carried out on a computer.

Preferred embodiments of the invention are defined in the dependent claims. It shall be understood that the claimed methods, processor, and computer program have similar and/or identical preferred embodiments as the claimed system and as defined in the dependent claims.

According to the present invention image data of the patient over time are obtained (e.g. using video actigraphy) and evaluated since it has been found that such a monitoring e.g. by use of video actigraphy has the advantage that movements of selected or all parts of the body can be measured without extra on-body sensors. Furthermore, local image analysis allows for a more detailed analysis of the context of the movement, going beyond mere activity counts. Such a monitoring thus provides a promising and unobtrusive method for capturing full-body motion of ICU patients and detecting thereof motoric alterations typical for delirium. Further, since the obtained image data generally capture the motion of the entire body, not only full-body movements can be analyzed but also activity of separate extremities.

The proposed monitoring system is an unobtrusive system. Delirious patients perform particular activity patterns which are reoccurring over time. Examples of these movements are picking of e.g. bed sheets and grabbing in the air. Preferably, the magnitude of the activity and the location of the activity (in which part of the body) are used according to the invention to check if delirium-prone movement patterns occur. Generally, potential activity parameters that may be evaluated according to the present invention include the duration, intensity, type, location and/or occurrence of delirium-typical motion events.

The proposed monitoring system calculates a delirium score based on the various measured activity parameters. This score can support clinical staff to detect and treat delirium in an early stage. With the currently used questionnaires patients are checked at most three times a day. With the proposed monitoring system it is possible to check scores and activity levels at any time, at regular intervals or continuously, of the day.

In a preferred embodiment said evaluation unit is configured to determine high and/or low movement counts of detected motion events and said delirium determination unit is configured to determine said delirium score from the duration of high or low movement counts and/or from the duration, intensity, type, location and/or occurrence of delirium-typical motion events. In this context "movement count" shall be understood as the intensity of motions of the patient. The larger/stronger the motions are, the higher is the movement count, which is sometimes also referred to as "activity count" or "activity level". Preferably, both the duration of high or low movement counts and the duration, intensity, type, location and/or occurrence of delirium-typical motion events are used to determine the delirium score, which provides a higher accuracy and reliability of the determined delirium score.

In another preferred embodiment said delirium determination unit is configured to determine said delirium score to indicate a higher likelihood and/or higher strength of delirium of the patient the longer, more intense and/or more often delirium-typical events occur.

Preferably, said delirium determination unit is configured to determine a delirium type indicator from the duration of high or low movement counts and/or from the duration, intensity, type, location and/or occurrence of delirium-typical motion events, said delirium type indicator indicating the type of delirium including hyperactive delirium, hypoactive delirium and mixed hyperactive and hypoactive delirium. The different motor subtypes are based on differences in motoric behavior. More knowledge about the subtype gives the opportunity to adjust the care for the patient. Currently it is not possible to detect the different subtypes of delirium in a continuous objective manner. Amongst others the amount of activity and speed of activity can give an indication about subtype of delirium. Additionally, classification of movement types beyond activity count and speed may give beneficial information.

Even more preferably, said delirium determination unit is configured to determine the delirium type indicator to indicate hyperactive delirium if the accumulated duration of hyperactive periods in a first time interval exceeds a first duration threshold and to determine the delirium type indicator to indicate hypoactive delirium if the accumulated duration of hypoactive periods in said first time interval exceeds a second duration threshold. In this context a hyperactive period is defined here as a period longer than a second time interval where the movement count (=activity count) exceeds a first movement count threshold. A hypoactive period is defined here as a period longer than a second time interval where the movement count falls below a second movement count threshold.

Advantageously, said delirium determination unit is configured to determine the delirium score to indicate non-delirium if there is a substantial difference of movement counts between day and night time and/or if the movement counts in a predetermined time interval are between a third and fourth movement count threshold. Said third and fourth movement count thresholds are preferably identical to the first and second, respectively, movement count thresholds. This embodiment provides for a higher accuracy of the delirium detection.

According to a preferred embodiment said monitoring unit is configured to continuously or at regular intervals obtain image data of the patient, in particular to obtain video data of the patient by use of a (conventional or infrared) video camera. Preferably, the same equipment as typically used in video actigraphy is used here. To monitor the patient also in darkness, an infrared camera, such as a near-infrared (NIR) camera or one or more image sensors is used in combination with NIR illumination.

Still further, in an embodiment the monitoring system further comprises an information determination unit for determining additional information about the patient from said image data and/or said detected motion events, said additional information including one or more of a mean activity of the patient in a predetermined time interval, detected motion patterns, motion events of predetermined parts of the patient's body and changes and/or trends of the patient's activity. Thus, in addition to the determined delirium score further information may be extracted from the obtained image data which might give an even better picture of the state of the patient to a nurse or a doctor. This additional information can be easily obtained from the obtained image data with the acquisition of additional image data.

In another embodiment said delirium determination unit is configured to determine said delirium score by additionally using additional physiological information about the patient, in particular EEG data and/or skin conductance data of the patient. The additional physiological information is obtained, simultaneously or in advance to the acquisition of the image data, by further equipment/hardware which may or may not part of the proposed monitoring system. For instance, in a preferred embodiment a physiological data acquisition unit is provided for acquiring additional physiological information about the patient, in particular EEG data and/or skin conductance data of the patient. Such a data acquisition unit may be a conventional unit for measuring EEG data of patients and/or a conventional skin conductance measurement unit (e.g. a NeXus Skin Conductance Sensor as e.g. currently described at http://www.mindmedia.nl/CMS/en/products/sensors/item/166-nx-gsrld.html and a NeXus EEG Sensor as e.g. currently described art http://www.mindmedia.nl/CMS/en/products/sensors/item/167-nx-exg2b.html).

The additional physiological information further increases the accuracy of the delirium detection and may be used to exclude motion that does not indicate or is not useful to evaluate for detecting delirium. For example, motoric alterations due to Parkinson disease can be excluded by means of EEG which can be used for detecting that a patient suffers from Parkinson disease.

For instance, in an embodiment said delirium determination unit is configured to compare said additional physiological information about the patient with reference physiological information indicative for delirium, in particular to compare EEG data and/or skin conductance data of the patient with typical patterns of EEG data and/or skin conductance data indicative for delirium. Preferably, said reference physiological information indicative for delirium is stored in a storage unit, such as a hard disc of a computer or a central storage, e.g. of a data management system as often provided in a hospital. Said reference physiological information may include typical patterns of EEG data and/or skin conductance data indicative for delirium. Thus, by this comparison the additional physiological information can be easily used to exclude motion that does not indicate or is not useful to evaluate for detecting delirium.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
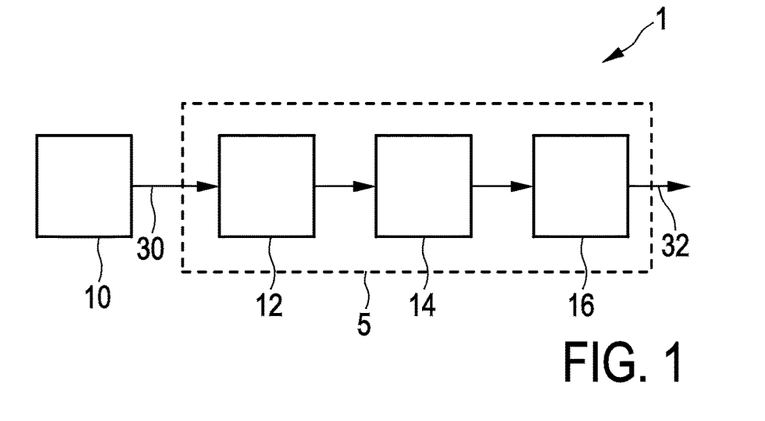
FIG. 1 shows a first embodiment of a monitoring system according to the present invention.

FIG. 1 shows a block diagram of a first embodiment of a monitoring system 1 according to the present invention. The monitoring system 1 comprises a monitoring unit 10 for obtaining image data 30 of the patient over time. Said monitoring unit 10 comprises, for instance, one or more image sensors or cameras for acquiring image data 30 (e.g. a new image at certain time intervals, for instance every second, or continuous video data). Further, the monitoring system 1 comprises an image analysis unit 12 for detecting motion events of the patient from the obtained image data, an evaluation unit 14 for classifying the detected motion events into delirium-typical motion events and non-delirium-typical motion events, and a delirium determination unit 16 for determining a delirium score 32 from the duration, intensity, type, location and/or occurrence of delirium-typical motion events, said delirium score indicating the likelihood and/or strength of delirium of the patient.

In an embodiment said image analysis unit 12, said evaluation unit 14 and said delirium determination unit 16 are implemented on a common processor 5, as indicated by the dashed box. Said processor 5 may implement each of said units 12, 14, 16 by a separate processing unit. Alternatively, in another embodiment several processors or a computer are used for implementing said units 12, 14, 16.

The proposed monitoring system enables a (semi-)automated, continuous and objective delirium detection, not only once but at regular intervals or continuously, as required e.g. for ICU patients. Movements of selected or all parts of the body can be monitored to provide an accurate determination of the delirium score 32 which is a simple measure for indicating the strength of delirium so that an alarm can be issued if a certain threshold is exceeded by the delirium score.

Figure 2:
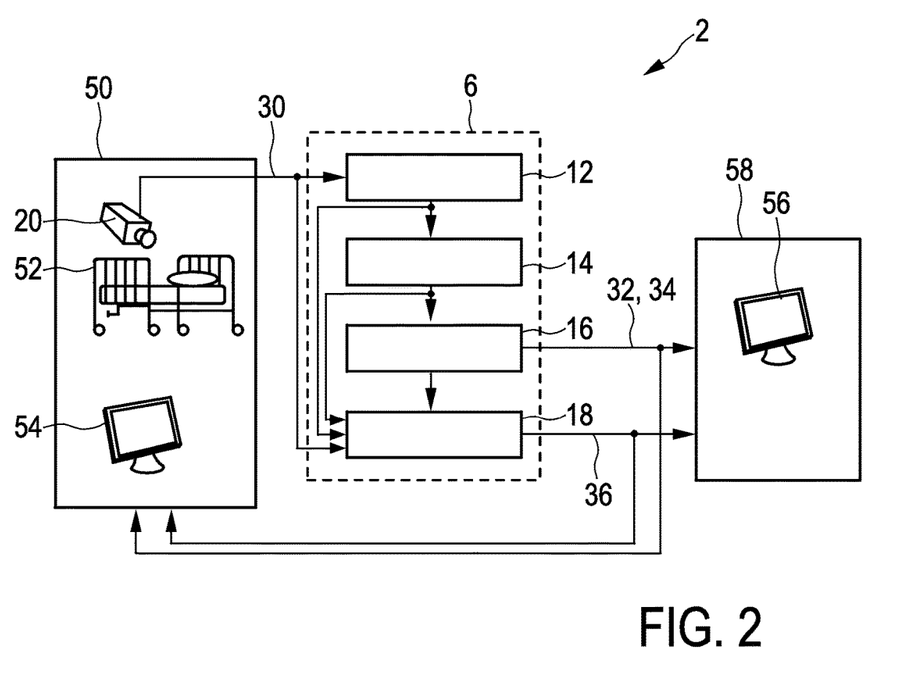
FIG. 2 shows a second embodiment of a monitoring system according to the present invention.

Another embodiment of a monitoring system 2 according to the present invention is schematically illustrated in FIG. 2. In this embodiment the monitoring system is installed in a hospital in which one or more (or all) patient rooms 50 are equipped with at least one camera 20 (representing said monitoring unit 10). The cameras 20 are mounted in such a manner that the whole body of a patient (not shown, but only the patient bed 52) is in picture. The video data 30 obtained by the camera 20 is transmitted to a computational system 6 (representing the processor 5) where the video data is analyzed. The activity is extracted real-time from the video data by the image analysis unit 12 and magnitude of activity, location of activity, type of activity (i.e. movement pattern) and/or time are stored. The video data 30, in particular detected motion events, is further analyzed by the evaluation unit 14 on typical patterns indicative for delirium, repetition of patterns, increase/decrease of activity, and/or speed of motion. Preferably, high and/or low movement counts of detected motion events are determined as well by the evaluation unit 14, said (high or low) movement counts indicating the intensity of motions of the patient. In addition the duration of high or low movement counts is determined for the determined movement counts.

The duration of high or low movement counts and/or the duration, intensity, type, location and/or occurrence of delirium-typical motion events are used by the delirium determination unit 16 to determine the delirium score. Preferably, both the duration of high or low movement counts and the duration, intensity, type, location and/or occurrence of delirium-typical motion events are used for this purpose, which provides a higher accuracy and reliability of the determined delirium score.

All this data can be calculated for the whole body or selected parts of the body such as the arms. Based on the different measures obtained from the video data and eventually other relevant information the delirium score is calculated.

The amount of activity and speed of activity is preferably used in addition to classify the subtype of delirium (hypoactive, hyperactive, mixed) and, preferably, to generate and output a corresponding delirium type indicator 34. Hyperactive delirium is detected if the accumulated duration of hyperactive periods in a first time interval exceeds a first duration threshold. Hypoactive delirium is detected if the accumulated duration of hypoactive periods in said first time interval exceeds a second duration threshold. Mixed delirium is detected if there is a shift between hypo- and hyperactivity. Non-delirium is detected if there is a substantial difference of movement counts between day and night time and/or if the movement counts in a predetermined time interval are between a third and fourth movement count threshold (which are preferably identical to the first and second threshold, respectively). Thus, generally, the delirium type indicator is determined from the duration of high or low movement counts and/or the duration, intensity, type, location and/or occurrence of delirium-typical motion events.

In an embodiment, the reference could be the activity of a non-delirious patient. If μ denotes the average movement count (=activity count) of a non-delirious patient during e.g. 24 hours (which is an example for the first time interval), then for example the first movement count threshold can be defined as μ+σ, where σ denotes the standard deviation, and the second movement count threshold can be defined as μ−σ. An example for the second time interval could be 5 minutes.

Similarly, the mentioned duration thresholds can be defined as follows: If d1 denotes the accumulated duration of all hyperactive periods of a non-delirious patient during e.g. 24 hours (=first time interval), then the first duration threshold can for example be defined as 2*d1 (i.e. at least twice the duration a non-delirious patient has). If d2 denotes the accumulated duration of all hypoactive periods of a non-delirious patient during e.g. 24 hours (=first time interval), then the second duration threshold can for example be defined as 2*d2.

Thus, a person can be judged as being a delirious patient if he/she shows a pronounced hyperactive behavior, a pronounced hypoactive behavior and/or significantly often delirium-typical movements.

The generated data, in particular the delirium score, is displayed on a bedside patient monitor 54 and/or a nurse monitor 56, preferably included in an overall overview of all patients that can be assessed at the nursing station 58. Based on thresholds set by the clinical staff an alarm can be given when the delirium score exceeds predefined thresholds.

Figure 3:
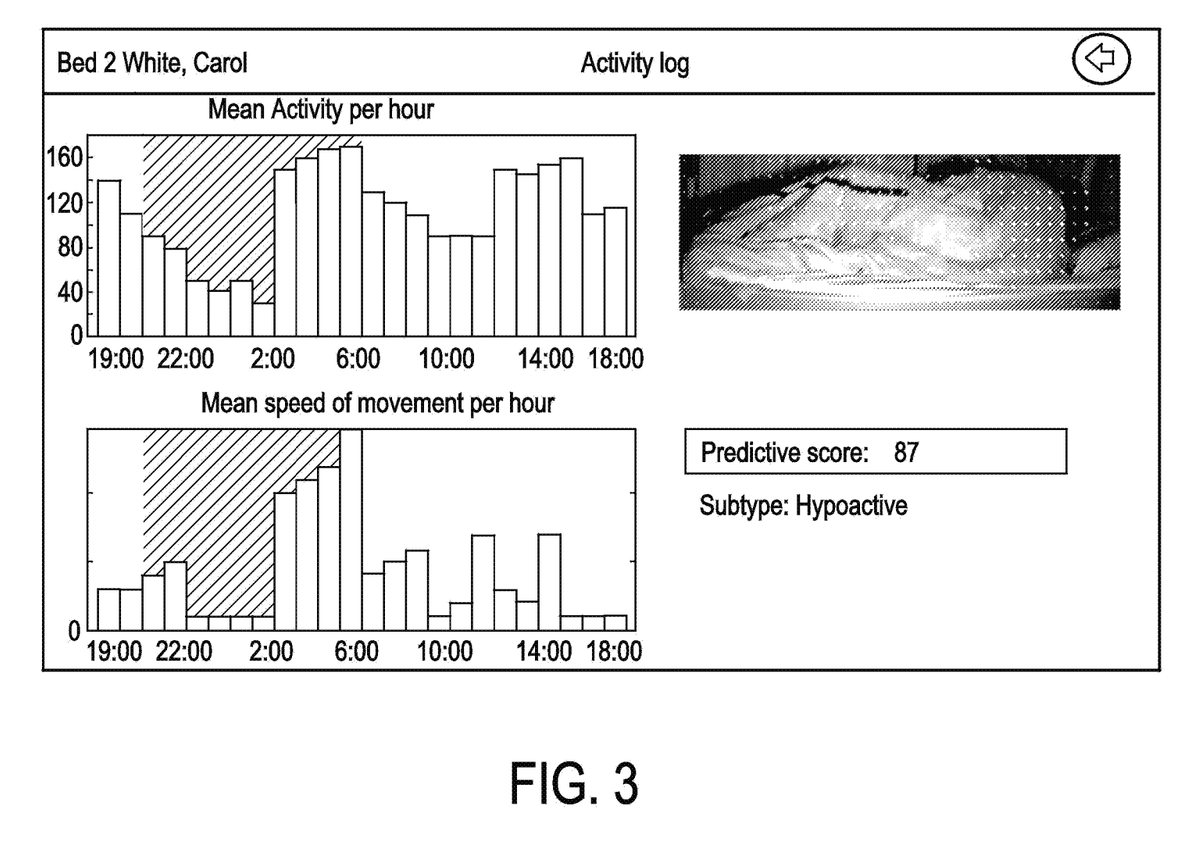
FIG. 3 shows a diagram illustrating information about a patient obtained by an embodiment of the proposed monitoring system.

Preferably, in this embodiment (but also in other embodiments), besides the delirium score clinical staff can access different parameters to have better insight in the patient condition. For this purpose an information determination unit 18 is provided for determining additional information 36 about the patient from said image data and/or said detected motion events. FIG. 3 shows an example of additional information data which can be assessed, the additional information data particularly including one or more of mean activity during the last 24 hours, mean speed of activity, current activity, but also patterns and how often these were repeated in the last 24 hours. The 24 hours analysis can also be adjusted to smaller or larger timeframes depending on the input of the clinical staff.

As shown in FIG. 3 the motion estimation is performed returning motion vectors (arrows in upper right image). The different motion within the body is well visible in different arrows of different orientation and length.

Figure 4:
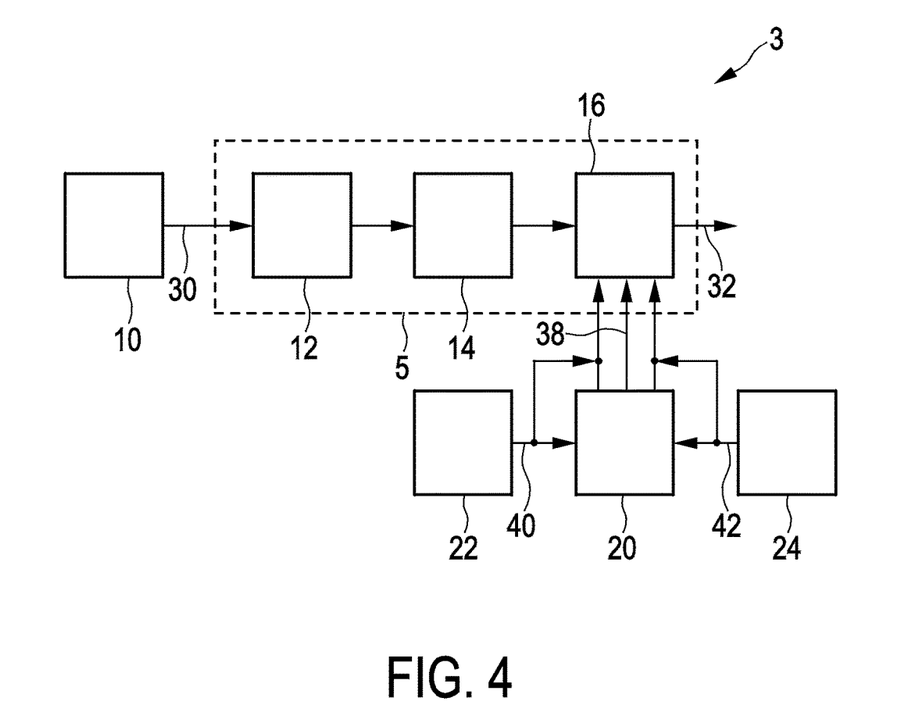
FIG. 4 shows a third embodiment of a monitoring system according to the present invention.

Still another embodiment of a monitoring system 3 according to the present invention is schematically shown in FIG. 4. In this embodiment relevant information from tests such as delirium prediction scores (e.g. PRE-DELIRIC score (as described in Van den Boogaard, M., Picckers, P., et al., PRE-DELIRIC, PREdiction of DELIRium in ICu patients; development and validation of a delirium prediction model for intensive care patients (2010), Proceedings of the European delirium Association, 5$^{th}$ scientific congress on delirium), CAM-ICU (Confusion Assessment Method—ICU) test results 38 can be filled and are input to the delirium determination unit 16 to calculate the delirium score 32. Said test results 38 are preferably stored in a separate storage unit 20.

Still further, in this embodiment the monitoring system 3 is further extended with EEG measurements 40. An association between clinical symptoms of delirium and changes in the spectral EEG is a consistent finding. EEG gives the possibility to measure real-time changes in brain functioning. Complementary information of EEG measurements can give more accurate information about the patient condition and a more precise delirium score. The EEG data 40 can be used to rule out changes in motoric behavior due to other diseases such as Parkinson or Epilepsy. Said EEG 40 may be pre-acquired and also stored in the storage unit 20. Alternatively, they may be acquired online by an EEG unit 22.

Similarly, in still another embodiment additional physiological information about the patient other than (or in addition to) EEG data may be used for determination of the delirium score 32. Particularly, skin conductance data 42 of the patient can be used to advantage for this purpose. Said skin conductance data 42 may also be stored in the storage unit 20 or may be acquired online by a skin conductance measurement unit 24.

Other additional physiological information that could be added for determining the delirium score may include vital signs, such as information about the heart rate, blood pressure, respiration rate. Such information may also be obtained from an analysis of the obtained image, e.g. using a known PPG (photo-plethysmography) algorithm. Alternatively, such information can be obtained by use of additional conventional equipment.

Preferably, in the delirium determination unit 16 said additional physiological information 40, 42 about the patient is compared with reference physiological information (e.g. stored also in the storage unit 20) indicative for delirium, in particular to compare EEG data and/or skin conductance data of the patient with typical patterns of EEG data and/or skin conductance data indicative for delirium. The result is preferably used to identify movement patterns which are not indicating delirium and can therefore be excluded from the determination of the delirium score. The use of such additional physiological information thus increases the accuracy and reliability of the delirium score determination.

In summary, the proposed monitoring system and method provides a simple, non-obtrusive, accurate and reliable way of determining the intensity of delirium of a patient. Preferred embodiments enable the determination of the type of delirium as well as additional information about the patient. The image data, particularly video data, obtained and evaluated according to the present invention also provides the possibility to analyze the types of movements in more detail to further increase the detection and classification of delirium. The invention is, however, not only able to return an activity count over time or a delirium score, but does further allow for a more distinguished analysis (e.g. location of hands, classifying the type of hand movement . . . ) depending on the desired application.

The proposed monitoring system and method can preferably be applied in all kinds of patient monitoring systems, as clinical decision support for delirium, in intensive care units, in general wards and in assisted living facilities.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A monitoring system for automated monitoring of a patient and detecting delirium of the patient, comprising:
   a monitoring unit for obtaining image data of the patient over time,
   an image analysis unit for detecting motion events of the patient from the obtained image data,
   an evaluation unit for classifying the detected motion events into delirium-typical motion events and non-delirium-typical motion events, wherein said evaluation unit is configured to determine high and/or low movement counts of detected motion events, and
   a delirium determination unit for determining a delirium score from the duration of high or low movement counts and/or the duration, intensity, type, location and/or occurrence of delirium-typical motion events, said delirium score indicating the likelihood and/or strength of delirium of the patient.

2. The monitoring system as claimed in claim 1, wherein said delirium determination unit is configured to indicate a higher likelihood and/or higher strength of delirium of the patient the longer, more intense and/or more often delirium-typical motion events occur.

3. The monitoring system as claimed in claim 1, wherein said delirium determination unit is configured to determine a delirium type indicator from the duration of high or low movement counts and/or from the duration, intensity, type, location and/or occurrence of delirium-typical motion events, said delirium type indicator indicating the type of delirium including hyperactive delirium, hypoactive delirium and mixed hyperactive and hypoactive delirium.

4. The monitoring system as claimed in claim 3, wherein said delirium determination unit is configured to determine the delirium type indicator to indicate hyperactive delirium if the accumulated duration of hyperactive periods in a first time interval exceeds a first duration threshold and to determine the delirium type indicator to indicate hypoactive delirium if the accumulated duration of hypoactive periods in said first time interval exceeds a second duration threshold.

5. The monitoring system as claimed in claim 1, wherein said delirium determination unit is configured to determine the delirium score to indicate non-delirium if there is a substantial difference of movement counts between day and night time and/or if the movement counts in a predetermined time interval are between a third and fourth movement count threshold.

6. The monitoring system as claimed in claim 1, wherein said monitoring unit is configured to continuously or at regular intervals obtain image data of the patient, in particular to obtain video data of the patient by use of a video camera.

7. The monitoring system as claimed in claim 1, further comprising an information determination unit for determining additional information about the patient from said image data and/or said detected motion events, said additional information including one or more of a mean activity of the patient in a predetermined time interval, detected motion patterns, motion events of predetermined parts of the patient's body and changes and/or trends of the patient's activity.

8. The monitoring system as claimed in claim 1, wherein said delirium determination unit is configured to determine said delirium score by additionally using additional physiological information about the patient, in particular Electroencephalography (EEG) data and/or skin conductance data of the patient.

9. The monitoring system as claimed in claim 8, wherein said delirium determination unit is configured to compare said additional physiological information about the patient with reference physiological information indicative for delirium, in particular to compare Electroencephalography (EEG) data and/or skin conductance data of the patient with typical patterns of Electroencephalography (EEG) data and/or skin conductance data indicative for delirium.

10. The monitoring system as claimed in claim 9, further comprising a storage unit for storing said reference physiological information indicative for delirium, in particular typical patterns of Electroencephalography (EEG) data and/or skin conductance data indicative for delirium.

11. The monitoring system as claimed in claim 8, further comprising a physiological data acquisition unit for acquiring additional physiological information about the patient, in particular Electroencephalography (EEG) data and/or skin conductance data of the patient.

12. A method for monitoring of a patient, comprising:
   obtaining image data of the patient over time,
   detecting motion events of the patient from the obtained image data,
   determining high and/or low movement counts of detected motion events,
   classifying the detected motion events into delirium-typical motion events and non-delirium-typical motion events, and
   determining a delirium score from the duration of high or low movement counts and/or the duration, intensity, type, location and/or occurrence of delirium-typical motion events, said delirium score indicating the likelihood and/or strength of delirium of the patient.

13. At least one processor for use in an automated monitoring system for monitoring a patient, said at least one processor being programmed to:
   detect motion events of the patient from image data obtained over time from the patient,
   classify the detected motion events into delirium-typical motion events and non-delirium-typical motion events and for determining high and/or low movement counts of detected motion events, and
   determine a delirium score from the duration of high or low movement counts and/or the duration, intensity, type, location and/or occurrence of delirium-typical motion events, said delirium score indicating the likelihood and/or strength of delirium of the patient.

14. A processing method for use in an automated monitoring system for monitoring a patient, said processing method comprising:
   detecting motion events of the patient from image data obtained over time from the patient,
   classifying the detected motion events into delirium-typical motion events and non-delirium-typical motion events and for determining high and/or low movement counts of detected motion events, and determining a delirium score from the duration of high or low movement counts and/or the duration, intensity, type, location and/or occurrence of delirium-typical motion events, said delirium score indicating the likelihood and/or strength of delirium of the patient.

15. A non-transitory storage medium storing instructions executable by a computer to carry out the steps of the processing method as claimed in claim 14 when said computer program is carried out on the computer.

16. The at least one processor of claim 13, further programmed to:

obtain the image data of the patient over time from a camera.

17. The at least one processor of claim 13, further programmed to:

determine, from the image data and/or the detected motion events, at least one of a mean activity of the patient in a predetermined time interval, detected motion patterns, motion events of predetermined parts of the patient's body and changes and/or trends of the patient's activity.

18. The at least one processor of claim 13, further programmed to:

determine the delirium score by additionally using at least one of acquired Electroencephalography (EEG) data and skin conductance data of the patient.

19. The at least one processor of claim 13, further programmed to:

compare the additional physiological information about the patient with at least one of Electroencephalography (EEG) data and skin conductance data of the patient with typical patterns of a corresponding one of Electroencephalography (EEG) data and skin conductance data indicative for delirium.

20. The at least one processor of claim 19, further programmed to at least one of:

store, in a storage, the typical patterns of Electroencephalography (EEG) data and/or skin conductance data indicative for delirium; and acquire, with a physiological data acquirer, Electroencephalography (EEG) data and/or skin conductance data of the patient.

* * * * *